United States Patent [19]
Suzukamo et al.

[11] 3,943,167
[45] Mar. 9, 1976

[54] PROCESS FOR PREPARING TRANS-CHRYSANTHEMIC ACID

[75] Inventors: Gohu Suzukamo, Ibaraki; Masami Fukao; Tsuneyuki Nagase, both of Takatsuki; Horosuke Toshioka, Ikeda, all of Japan

[73] Assignee: Sumitomo Chemical Company, Limited, Japan

[22] Filed: Nov. 13, 1973

[21] Appl. No.: 415,348

[30] Foreign Application Priority Data
Nov. 13, 1972 Japan.............................. 47-113634

[52] U.S. Cl............................ 260/514 H; 260/468 H
[51] Int. Cl.².......................................... C07C 51/42
[58] Field of Search...................... 260/514 H, 468 H

[56] References Cited
UNITED STATES PATENTS
3,046,299  7/1962  Julia.................................. 260/468

3,538,143  11/1970  Matsui et al........................ 260/468

OTHER PUBLICATIONS
Eliel et al., JACS 83, 2351 (1961).
Eliel, Stereochemistry of Carbon Compounds, 222–224 (1962).
Patai, The Chemistry of Carboxylic Acids and Esters, 521–523 (1969).

Primary Examiner—Robert Gerstl
Attorney, Agent, or Firm—Stewart and Kolasch

[57] ABSTRACT

A process for preparing trans-chrysanthemic acid which comprises reacting a mixture of alkyl trans-chrysanthemate and alkyl cis-chrysanthemate with an equimolar amount or less of an alkali with respect to the trans-isomer in the presence of water or an alcohol to hydrolyze the trans-isomer predominantly and separating the hydrolyzed trans-isomer from the unreacted cis-isomer.

6 Claims, No Drawings

PROCESS FOR PREPARING TRANS-CHRYSANTHEMIC ACID

The present invention relates to a process for preparing trans-chrysanthemic acid, i.e. 2,2-dimethyl-3-(2'-methyl)-1'-propenyl-1-1,3-trans-cyclopropane-1-carboxylic acid. More particularly, it relates to a process for the selective production of trans-chrysanthemic acid from a mixture of alkyl trans-chrysanthemate, i.e. alkyl 2,2-dimethyl-3-(2'-methyl)-1'-propenyl-1,3-trans-cyclopropane-1-carboxylate, and alkyl cis-chrysanthemate, i.e. alkyl 2,2-dimethyl-3-(2'-methyl)-1'-propenyl-1,3-cis-cyclopropane-1-carboxylate.

It is known that chrysanthemic acid is the acid component of the esters of the so-called "pyrethroidal insecticides" such as pyrethrin, allethrin, phthalthrin and 5-benzyl-3-furylmethyl chrysanthemate. It is also known that the pyrethroids having the residue of trans-chrysanthemic acid as the acid component generally exhibit a higher insecticidal activity than those having the residue of cis-chrysanthemic acid as the acid component. Thus, the use of the trans-isomer of chrysanthemic acid for the production of pyrethroids is more advantageous and favorable than that of the corresponding cis-isomer.

For the production of alkyl chrysanthemate, there has heretofore been widely adopted the reaction of 2,5-dimethyl-2,4-hexadiene with alkyl diazoacetate. However, the product in this reaction is a mixture of alkyl cis-chrysanthemate and alkyl trans-chrysanthemate. Therefore, it is necessary to separate the trans-isomer from the said mixture and to convert the cis-isomer into the corresponding trans-isomer from the industrial viewpoint. Since the boiling point of alkyl trans-chrysanthemate is extremely close to that of the corresponding cis-isomer, the separation of these isomers by fractional distillation is not easy.

Hitherto, the separation of the trans-isomer and the cis-isomer has usually been carried out in the free acid form rather than in the alkyl ester form. Thus, a number of methods have been proposed for the separation of trans-chrysanthemic acid and cis-chrysanthemic acid. Some typical examples of them are as follows: recrystallization using appropriate solvents [J.Chem. Soc., 1945, 283]; heating a mixture of the trans-isomer and the cis-isomer with a large amount of dilute sulfuric acid [Bull.Agr.Chem.Japan, 19, 159 (1955)]; selective lactonization of the cis-isomer in the presence of an acid catalyst under anhydrous conditions so as to separate the trans-isomer [Japanese Pat. No. 13898/1972], etc. However, these methods are each defective, for instance, in requiring troublesome operations, taking a long period of time, necessitating the lactonization of the cis-isomer and the like problems. Eventually, these methods all involve the separation of trans-chrysanthemic acid and cis-chrysanthemic acid from the mixture thereof based upon the difference of solubility in an appropriate solvent or with the possibility of lactonization of the cis-isomer according to its geometrical structure.

It has now unexpectedly been found that, when treated with an alkali under certain conditions, alkyl trans-chrysanthemate and alkyl cis-chrysanthemate are hydrolyzed in different rates with respect to each other. It has also been found that, by the utilization of such a difference in the hydrolyzing rate, alkyl trans-chrysanthemate can be predominantly hydrolyzed to the corresponding free acid, which may be readily separated from unreacted alkyl cis-chrysanthemate. The present invention is based on these findings.

In this connection, it may be noted that no attempt has ever been made to separate alkyl trans-chrysanthemate by utilization of the difference in the reaction rate between the trans-isomer and the cis-isomer in a reaction in which both of them can participate. It may be also noted that no procedure for efficiently separating a trans-isomer or a cis-isomer from its mixture with the other isomer by utilization of the difference in the reaction rate in the esterification of the free acids or in the hydrolysis of the alkyl esters has ever been proposed in this field.

According to the present invention, there is provided a process for preparing trans-chrysanthemic acid which comprises reacting a mixture of alkyl trans-chrysanthemate and alkyl cis-chrysanthemate with an equimolar amount or less of an alkali with respect to the trans-isomer in the presence of water and/or an alcohol to hydrolyze the trans-isomer predominantly and separating the hydrolyzed trans-isomer from the unreacted cis-isomer.

The alkyl trans-chrysanthemate and the alkyl cis-chrysanthemate are respectively represented by the formulae:

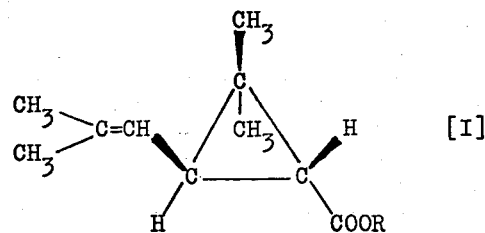

and

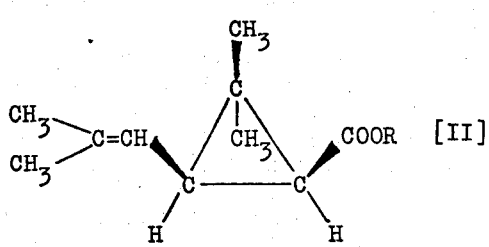

wherein R is a lower alkyl group. The term "lower alkyl" hereinabove used is usually intended to mean alkyl groups having 1 to 8 carbon atoms and includes specifically methyl, ethyl, n-propyl, isopropyl, n-butyl, isobutyl, t-butyl, etc. Particularly preferred are methyl and ethyl. In the present invention, a mixture of the trans-isomer [I] and the cis-isomer [II] in an optional proportion is used as a starting material.

The alkali to be used in the invention may be those usually employed for hydrolysis. An alkali metal hydroxide and an alkali metal alcoholate are preferable. Examples of the alkali metal hydroxide are lithium hydroxide, sodium hydroxide and potassium hydroxide. The use of sodium hydroxide or potassium hydroxide is industrially advantageous. As the alkali metal alcoholate, there may be used any one selected from alkali metal primary alcoholates, alkali metal secondary alcoholates and alkali metal tertiary alcoholates. The use of sodium methylate or sodium ethylate is favorable from the economical viewpoint.

The alkali is required to be used in an approximately equimolar amount or less with respect to the trans-isomer in the starting material. Preferably, the amount of the alkali may be 0.5 to 1 mole per 1 mole of the trans-isomer. Under such condition, the trans-isomer is predominantly hydrolyzed. The use of the alkali in an amount larger than an equimolar amount with respect to the trans-isomer and the interruption of the hydrolysis at a certain stage may result in the production of trans-chrysanthemic acid while maintaining the cis-isomer unreacted to a certain extent, the selectivity is much inferior and the selection of appropriate reaction conditions is difficult.

The reaction of a mixture of the two isomeric esters with the alkali is carried out in the presence of water or an alcohol. As the alcohol, there may be employed any one of primary alcohols, secondary alcohols, and tertiary alcohols, but the use of a primary alcohol such as methyl alcohol or ethyl alcohol is economically desirable. If desired, there may be used any appropriate solvent inert to the reaction in addition to water and/or the alcohol.

The reaction is normally effected at a temperature of from about 10°C to the refluxing temperature of the reaction system, preferably from 10°C to 150°C. When a lower reaction temperature is adopted, the selectivity to the trans-isomer becomes increased, but a longer reaction time is required.

The progress of the reaction may be checked by analyzing the produced acid or the unreacted ester in the reaction mixture in a per se conventional manner such as gas chromatography or IR absorption spectrum.

In the reaction mixture thus obtained, there are included the hydrolyzed product of alkyl trans-chrysanthemate, i.e. trans-chrysanthemic acid, and the unhydrolyzed alkyl cis-chrysanthemate. Trans-Chrysanthemic acid is quite soluble in an aqueous alkaline solution in the form of the carboxylate ion. On the other hand, alkyl cis-chrysanthemate is not soluble in water and can be dissolved in organic solvents such as ether, benzene, toluene and hexane. Therefore, the said reaction mixture, which is alkaline, may be treated with an appropriate water-immiscible organic solvent in the presence of water, whereby trans-chrysanthemic acid is retained in the aqueous layer and alkyl cis-chrysanthemate is extracted in the organic solvent layer. When desired, the reaction mixture may be concentrated to remove the reaction medium and/or the alcohol produced in the course of the hydrolysis prior to the treatment with the organic solvent. For recovery of the trans-chrysanthemic acid from the water layer, it may be made acidic with a mineral acid such as sulfuric acid or hydrochloric acid to separate the free trans-chrysanthemic acid, which may be recovered by a conventional procedure such as extraction. The alkyl cis-chrysanthemate in the organic solvent layer may be subjected to epimerization to produce the corresponding trans-isomer.

Practical and presently preferred embodiments of the present invention are illustratively shown in the following Examples wherein % and the cis/trans ratio are indicated by weight.

EXAMPLE 1

In a 300 ml volume four-necked flask equipped with a stirrer, a thermometer and a reflux condenser, there were charged ethyl chrysanthemate consisting of 35.2 % of the cis-isomer and 64.8 % of the trans-isomer (100 g; trans-isomer, 0.33 mol) and a 25 % aqueous solution of sodium hydroxide (48 g; NaOH, 0.30 mol), and the mixture was stirred at 85°C for 4 hours. After distilling off ethanol produced during the hydrolysis, the reaction mixture was admixed with water (200 g) and extracted with n-hexane (60 g) two times. The n-hexane layer was separated, washed, dried and evaporated, and the residue was distilled under reduced pressure to give unreacted ethyl chrysanthemate (41.3 g; cis/trans = 55.4/44.6). B.P. 112 to 116°C/19 mmHg.

The water layer was made acidic with sulfuric acid and extracted with toluene (80 g) two times. The toluene layer was washed and evaporated, and the residue was distilled under reduced pressure to give trans-chrysanthemic acid (47.1 g; trans-isomer, 80.5 %). B.P. 110° to 114°C/2 mmHg.

EXAMPLE 2

In a 500 ml volume four-necked flask, there were charged ethyl chrysanthemate consisting of 33.6 % of the cis-isomer and 66.4 % of the trans-isomer (100 g; trans-isomer, 0.34 mol), a 25 % aqueous solution of sodium hydroxide (30 g; NaOH, 0.19 mol) and ethanol (50 g), and the mixture was stirred at 60°C for 5 hours as in Example 1. After removing ethanol by distillation, the reaction mixture was treated as in Example 1 to give trans-chrysanthemic acid (28.7 g; trans-isomer, 90.0 %) and unreacted ethyl chrysanthemate (64.0 g; cis/trans = 53.8/46.2).

Example 3

In a 500 ml volume four-necked flask, there were charged ethyl chrysanthemate consisting of 33.6 % of the cis-isomer and 66.4 % of the trans-isomer (100 g; trans-isomer, 0.34 mol), water (50 g), ethanol (200 g) and potassium hydroxide (20.0 g; 0.35 mol), and the mixture was stirred at 50°C for 6 hours as in Example 1. The reaction mixture was treated as in Example 1 to give unreacted ethyl chrysanthemate (45.0 g; cis/trans = 52.8 /47.2) and trans-chrysanthemic acid (45.4 g; trans-isomer, 84 %).

EXAMPLE 4

As in Example 1, ethyl chrysanthemate consisting of 9.9 % of the cis-isomer and 90.1 % of the trans-isomer (100 g; trans-isomer, 0.46 mol) and a 25 % aqueous solution of sodium hydroxide (65.2 g; 0.40 mol) were reacted at 85°C for 3 hours. The reaction mixture was treated as in Example 1 to give unreacted ethyl chrysanthemate (27.0 g; cis/trans=25.6/74.4) and trans-chrysanthemic acid (59.3 g; trans-isomer, 97.0 %).

EXAMPLE 5

Ethyl chrysanthemate consisting of 35.6 % of the cis-isomer and 64.4 % of the trans-isomer (10 g; trans-isomer, 0.033 mol) was treated with ethanol (30 g) and sodium ethylate (2.3 g; 0.033 mol) at the boiling temperature of ethanol for 2 hours. After the removal of ethanol by distillation, the reaction mixture was admixed with water (30 g) and extracted with ether (20 g) two times. The ether layer was washed, dried and evaporated, and the residue was distilled under reduced pressure to give unreacted ethyl chrysanthemate (4.7 g; cis/trans = 50.0/50.0). B.P. 115° to 120°C/24 mmHg.

The water layer was made acidic with sulfuric acid and extracted with toluene (20 g) two times. The toluene layer was washed and distilled under reduced pressure to give trans-chrysanthemic acid (4.2 g; trans-isomer, 80.0 %). B.P. 122° to 130°C/3.3 mmHg.

EXAMPLE 6

In a 100 ml volume four-necked flask, there were charged methyl chrysanthemate consisting of 40.0 % of the cis-isomer and 60.0 % of the trans-isomer (20.0 g; trans-isomer, 0.066 mol), a 10 % aqueous solution of potassium hydroxide (33 g; 0.059 mol) and methanol (20 g), and the mixture was stirred at 50°C for 4 hours as in Example 1. After the removal of methanol by distillation, the reaction mixture was treated as in Example 4 to give trans-chrysanthemic acid (9.4 g; trans-isomer, 83 %) and unreacted methyl chrysanthemate (9.6 g).

What is claimed is:

1. A process for preparing an enriched trans-chrysanthemic acid from a mixture of alkyl trans-chrysanthemate and alkyl cis-chrysanthemate which comprises reacting said mixture with an alkali metal hydroxide or an alkali metal alcoholate in an amount of from 0.5 to 1 mole based on 1 mole of the trans-isomer in the presence of water or an alcohol at a temperature of from 10° to 150° C to hydrolyze the trans-isomer predominantly and separating the hydrolyzed product from the unreacted alkyl chrysanthemate to obtain an enriched trans-chrysanthemic acid.

2. The process according to claim 1, wherein the alkali metal hydroxide is sodium hydroxide or potassium hydroxide.

3. The process according to claim 1, wherein the alkali metal alcoholate is sodium methylate or sodium ethylate.

4. The process according to claim 1, wherein the alcohol is methyl alcohol or ethyl alcohol.

5. The process according to claim 1, wherein the separation of the hydrolyzed trans-isomer is effected by treatment of the reaction mixture with a water-immiscible organic solvent which can dissolve the unhydrolyzed cis-isomer in the presence of water under an alkaline condition.

6. A process for preparing an enriched trans-chrysanthemic acid from a mixture of alkyl trans-chrysanthemate and alkyl cis-chrysanthemate which comprises the step of (1) reacting said mixture with an alkali metal hydroxide or an alkali metal alcoholate in an amount of from 0.5 to 1 mole based on 1 mole of the trans-isomer at a temperature of from 10° to 150° C to hydrolyze the trans-isomer predominantly, (2) separating the hydrolyzed product from the unreacted alkyl chrysanthemate to obtain an enriched trans-chrysanthemic acid and (3) epimerizing the alkyl cis-chrysanthemate in the unreacted alkyl chrysanthemate and recycling the epimerized product to step (1).

* * * * *